United States Patent [19]
Goldsmith

[11] Patent Number: 5,275,561
[45] Date of Patent: Jan. 4, 1994

[54] METHOD FOR PREPARING TOOTH STRUCTURE FOR BONDING

[75] Inventor: Daniel S. Goldsmith, West Bloomfield, Mich.

[73] Assignee: American Dental Laser, Inc., Troy, Mich.

[21] Appl. No.: 862,968

[22] Filed: Apr. 3, 1992

[51] Int. Cl.$^5$ .................... A61C 15/00; A61C 5/00
[52] U.S. Cl. ..................... 433/216; 433/215
[58] Field of Search ................ 433/215, 216, 217

[56] References Cited

U.S. PATENT DOCUMENTS

| | | | |
|---|---|---|---|
| 4,174,571 | 11/1979 | Gallant | 433/216 |
| 4,412,402 | 11/1983 | Gallant | 51/439 |
| 4,522,597 | 6/1985 | Gallant | 433/216 |
| 4,595,365 | 6/1986 | Edel et al. | 433/216 |
| 4,776,794 | 10/1988 | Meller | 433/216 |
| 4,969,868 | 11/1990 | Wang | 604/20 |
| 5,094,615 | 3/1992 | Bailey | 433/88 |
| 5,094,839 | 3/1992 | Lowder et al. | 424/49 |

*Primary Examiner*—Robert P. Swiatek
*Assistant Examiner*—Cindy A. Cherichetti
*Attorney, Agent, or Firm*—Gifford, Groh, Sprinkle, Patmore and Anderson

[57] ABSTRACT

The present invention discloses a method for preparing tooth structure, such as dentin and enamel, for bonding with a composite material. The method includes the steps of creating a fluid stream laden with an abrasive material, such as aluminum oxide. The fluid stream is directed towards the tooth structure so that the abrasive material laden fluid stream impinges upon the tooth structure and roughens it for enhanced bonding with composite material.

17 Claims, 2 Drawing Sheets

METHOD FOR PREPARING TOOTH STRUCTURE FOR BONDING

BACKGROUND OF THE INVENTION

I. Field of the Invention

The present invention relates generally to dental procedures and, more particularly, to a dental procedure for preparing tooth structure for bonding with composite material.

II. Description of the Prior Art

When decay is removed from tooth structure, such as dentin and enamel, the resulting cavity caused by the removal of the tooth decay must be filled in order to protect the tooth from further decay, infection and the like. Both amalgam and composites have been used to fill the cavity preparation performed by the dentist.

When amalgam is used to fill the cavity preparation performed by the dentist, the dentist typically undercuts the enamel thus forming a pocket in the tooth having a relatively small opening exposed to the exterior of the enamel. Amalgam is then forced into the pocket and is held in place by a mechanical retention with the tooth structure. Although amalgam has proven adequate in filling cavity preparations, it is cosmetically undesirable due to its silver or dark color.

There are, however, composites and other similar materials (hereinafter collectively referred to as composites or composite materials) which are of the same color as the tooth and are used to fill the cavity preparation performed by the dentist when removing the tooth decay. Since these composites are of the same color as the tooth, they are cosmetically more desirable than amalgam.

In order to prepare the tooth structure, i.e. the enamel and dentin and associated tooth material, an acid is typically used to etch the enamel to enhance the bond between the composite and the enamel. The dentin, however, should not be etched because of problems with pulpal insult from acid which can result in increased pulpal sensitivity and other complications.

Consequently, in order to protect the dentin from the acid etch, the dentin is first covered with a primer which not only protects the dentin from the acid during a subsequent enamel etch, but also removes the smear layer caused by the traditional rotary drill used by dentists.

After the dentin has been coated with the primer, an acid etch is then used to etch the enamel surrounding the opening in the tooth structure. FIG. 1 depicts such an acid etch at approximately 3500 magnification. As can be seen from FIG. 1, the acid etch in the enamel caused large crevices and peaks in the enamel.

After the acid etch, the acid is rinsed away with water and the tooth is dried. After drying, a bonding agent is applied to both the dentin as well as the etched enamel. The composite is then applied to the dentin and etched enamel on top of the bonding agent, cured with a light whereupon the composite restoration is completed.

There are, however, a number of disadvantages with this previously known process for cavity preparation for composites. One disadvantage is that the entire procedure for cavity preparation using a composite is a time consuming and relatively difficult procedure for the dentist.

A still further disadvantage of the previously known procedure is that it is very difficult, if not altogether impossible, for the dentist to apply the primer only to the dentin while leaving the enamel surrounding the cavity preparation exposed for the subsequent acid etch. This is particularly true since the dentin-enamel junction forms only a fine line oftentimes difficult for the dentist to see. Consequently, as a practical matter, the bonding is applied by the dentist not only to the dentin but also to portions of the enamel. Any primer applied to the enamel, however, will prevent the desired acid etch of the enamel and thus degrade the overall integrity of the bonding between the enamel and the composite.

A still further disadvantage of the previously known cavity preparation for composites is that the acid etch creates relatively deep crevices and high peaks in the area of the enamel which is etched as shown in FIG. 1.

While the deep crevices and high peaks of the enamel caused by the acid etch enhance the overall bond between the composite and the enamel, moisture from the rinse following the acid etch can become entrapped in the crevices. Any remaining moisture entrapped within the crevices of the acid etch from insufficient drying weakens the bond between the composite and the enamel.

A still further disadvantage of these previously known cavity preparations for composites is that the polymerization process of the composite places varying magnitudes of stress upon the bond between the dentin and the composite. Such stresses can result in increased sensitivity between the composite and the dentin, especially where gaps exist between the composite and the dentin. Such gaps can result in small movement of the composite when the patient chews or otherwise applies pressure to the composite which also results in increased sensitivity for the tooth.

A still further disadvantage of the previously known cavity preparation using acid etch on the enamel is that gaps frequency result between the composite and the enamel due to the large peaks and valleys in the enamel from the acid etch. These gaps increase the risk of microleakage which allows contaminants to infiltrate the gaps in the enamel and cause additional decay of the tooth from the microleakage.

SUMMARY OF THE PRESENT INVENTION

The present invention provides a method for cavity preparation for composites and similar materials which overcomes all of the above mentioned disadvantages of the previously known methods.

In brief, the present invention comprises the step of creating a fluid stream laden with abrasive material. Preferably aluminum oxide is utilized as the abrasive material and the aluminum oxide has an average size of between 2 and 100 microns. Although any fluid can be used, preferably air is used.

The abrasive material laden fluid stream is then directed towards the tooth structure, i.e. both the enamel and the dentin, so that the stream laden with abrasive material impinges upon the tooth structure and roughens it. Furthermore, by maintaining the impingement of the abrasive material laden fluid stream on the dentin for a sufficient time, the stream appears to close the a tubules in the dentin thereby resulting in decreased tooth sensitivity.

Following roughening of the tooth structure by the abrasive material laden stream, the dentist applies both the bonding and the composite to the tooth structure and cures the composite in the conventional fashion thus completing the tooth restoration.

BRIEF DESCRIPTION OF THE DRAWING

A better understanding of the present invention will be had upon reference to the following detailed description when read in conjunction with the drawing in which.

DETAILED DESCRIPTION OF A PREFERRED EMBODIMENT OF THE PRESENT INVENTION

The present invention provides an improved method for surface modification and preparation following removal of tooth decay for use with composite restorations. Furthermore, as used herein, the term composites includes veneers, resins, glass ionomers, ceramics, porcelain and similar materials. Such materials are typically attached to the tooth by a bonding material, as well as mechanical adhesion to the teeth structure.

Figure 3:
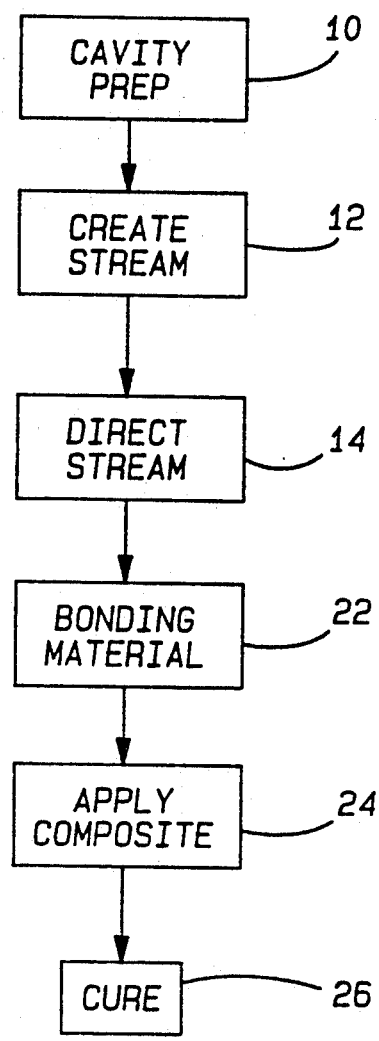
FIG. 3 is a flow chart illustrating the preferred embodiment of the present invention.

With reference now to FIG. 3, the dentist first performs a cavity preparation at step 10 in order to prepare the cavity for subsequent bonding with the composite. The cavity preparation at step 10, i.e. removal of the tooth decay, can be performed either conventionally, such as with a rotary drill, or through other means, such as with a laser, an air abrasive system or the like.

Following the cavity preparation at step 10, both the dentin and a portion of the enamel surrounding the opening in the tooth are exposed. It is this opening and adjacent enamel (not shown) which will be subsequently filled and/or covered by the composite.

In accordance with the present invention, following the cavity preparation at step 10, a fluid stream laden with abrasive material is created or initiated by the dentist at step 12 using any conventional equipment. Such equipment typically uses air as the fluid and aluminum oxide as the abrasive material. Typically, pressurized air is used to create the air flow and preferably the pressure of the pressurized air is variably controlled by the dentist between 20-200 psi. The aluminum oxide of the present invention has an average size of between 2 and 100 microns although other types and sizes of abrasive material can alternatively be used.

After creating or initiating the abrasive material laden fluid stream, the dentist directs the abrasive material laden fluid stream toward the tooth structure at step 14 which will undergo restoration with a composite. Furthermore, the dentist directs the fluid stream so that the abrasive material impinges on the tooth structure, i.e. dentin and surrounding enamel, which roughens the tooth structure in preparation for the composite.

Figure 1:
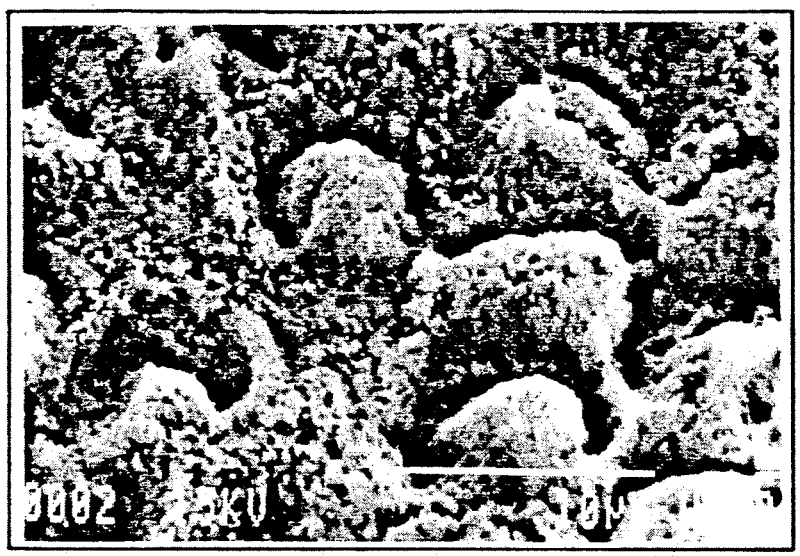
FIG. 1 is a microphotograph illustrating an acid etched enamel at approximately 3500 magnification.
Figure 2:
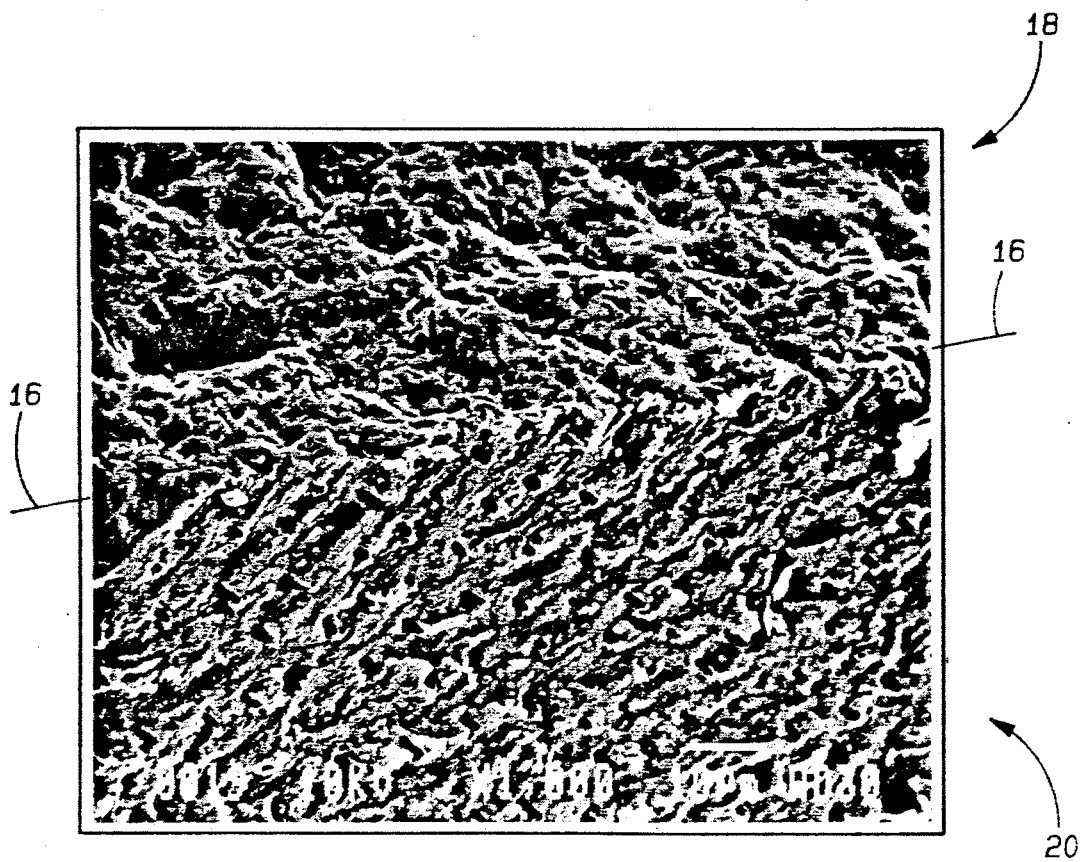
FIG. 2 is a microphotograph illustrating the effect of cavity preparation in accordance with the present invention.

With reference now to FIG. 2, the portion of FIG. 2 above line 16 indicated by arrow 18 illustrates tooth structure roughened by an abrasive laden fluid stream in accordance with the present invention. As can be seen from area 18 of FIG. 2, the tooth structure, while roughened by the abrasive material, does not exhibit the deep peaks and valleys of a conventional acid etch such as shown in FIG. 1. Furthermore, the area 18 roughened in accordance with the present invention includes not only the enamel, but also the dentin.

Still referring to FIG. 2, the area 20 below the line 16 illustrates dentin which is unmodified by the abrasive material laden fluid stream. As illustrated in area 20, the tubules in the dentin are exposed to the surface of the dentin. In sharp contrast to this, the area 18 roughened by the abrasive material appears to close or otherwise cover the tubules and it is believed that this results in decreased sensitivity of the dentin.

With reference again to FIG. 3, after the tooth structure including both the dentin and the enamel have been roughened at step 14, the dentist then applies a bonding material to the tooth structure at step 22 and subsequently applies the composite to the bonding material at step 24. The composite is then cured at step 26 and the restoration is completed.

The method of the present invention thus achieves numerous advantages over the previously known methods for bonding composites to tooth structure. First, since the acid etch of the enamel is completely eliminated, it is no longer necessary for the dentist to protect the dentin by coating the dentin with a primer prior to the acid etch. This not only saves time for the dentist, but also eliminates the previously known problem of unintentionally applying the primer to areas of the enamel where etching was desired.

A still further advantage of the present invention is that, since the acid etch has been eliminated, it is no longer necessary to wash the acid from the tooth structure following the acid etch. As such, with the present invention, it is no longer necessary to dry the tooth structure of water following the surface modification of the tooth structure. Likewise, since the water a rinse has been eliminated, the likelihood of entrapped moisture on the tooth structure and the previously known resulting degradation of the composite bond is also eliminated.

A still further advantage of the present invention is that the composite material is bonded not only to the enamel as in the previously known methods, but also to the dentin. Such bonding of the composite to the dentin effectively eliminates any gaps which may be present between the composite and the dentin thus performing a firmer bond and support between the composite and the dentin. This firmer bond reduces the likelihood of sensitivity caused by small movement of the composite relative to the dentin.

It is believed that a still further advantage of the present invention is that the abrasive material effectively closes the tubules present in the dentin prior to restoration of the tooth. By closing the tubules, the likelihood of sensitivity of the tooth is further diminished.

Furthermore, the relatively small peaks and valleys, as contrasted with an acid etch, caused by the method of the present invention in the enamel and dentin reduces the possibility of microleakage through gaps between the composite and the tooth structure. This not only provides a better bond between the composite and the tooth structure, but also minimizes the risk of microleakage.

From the foregoing, it can be seen that the present invention provides a novel method for cavity preparation for composites. It has also been found that by using a less abrasive material, such as sodium bicarbonate, entrained in the fluid stream, the fluid stream with the less abrasive material can be used to clean teeth, remove plaque and tartar and the like. As with the cavity preparation, the sodium bicarbonate is preferably entrained within an air flow stream. Having described my invention it can be seen that the present invention provides a novel means of preparing a cavity preparation for composites, as well as cleaning teeth. Having described my invention, however, many modifications thereto will become apparent to those skilled in the art to which it pertains without deviation from the spirit of the invention as defined by the scope of the appended claims.

I claim:

1. A method for preparing a tooth structure for bonding with a composite material comprising the steps of:
   creating a fluid stream laden with abrasive material,
   directing said fluid stream towards the tooth structure for a time sufficient so that the abrasive material laden fluid stream impinges upon the tooth structure and roughens the tooth structure wherein said creating step comprises the step of variably metering abrasive material into the fluid stream, and
   wherein said metering step comprises the step of metering between one gram per minute and fifteen grams per minute of abrasive material into the fluid stream.

2. The invention as defined in claim 1 wherein said tooth structure comprises dentin and enamel wherein said directing step comprises the step of directing the impingement of the abrasive material laden fluid stream against both the enamel and the dentin.

3. The invention as defined in claim 1 wherein said abrasive material comprises aluminum oxide.

4. The invention as defined in claim 3 wherein said abrasive material has an average size of between two and one hundred microns.

5. The invention as defined in claim 1 wherein said fluid is air.

6. The invention as defined in claim 5 wherein said step of creating a fluid stream comprises the step of using a compressed air source and varying the pressure of the compressed air source.

7. The invention as defined in claim 6 wherein said pressure varies from twenty to two hundred psi.

8. The invention as defined in claim 1 wherein said tooth structure includes exposed tubules and further comprising the step of maintaining impingement of the abrasive material laden fluid stream on the tooth structure for a time sufficient to close said tubules.

9. The invention as defined in claim 1 wherein said abrasive material comprises sodium bicarbonate powder.

10. A method for restoration of tooth structure using a composite comprising the steps of:
    creating a fluid stream laden with abrasive material,
    directing said fluid stream towards the tooth structure for a time sufficient so that the abrasive material laden fluid stream impinges upon the tooth structure and roughens the tooth structure,
    thereafter applying a bonding material on the tooth structure that has been roughened,
    thereafter applying composite to the bonding material, and
    curing the bonding material.

11. The invention as defined in claim 10 wherein said bonding material applying step is performed immediately following said directing step.

12. The invention as defined in claim 10 wherein said tooth structure comprises dentin and enamel wherein said directing step comprises the step of directing the impingement of the abrasive material laden fluid stream against both the enamel and the dentin.

13. The invention as defined in claim 10 wherein said abrasive material comprises aluminum oxide.

14. The invention as defined in claim 13 wherein said abrasive material has an average size of between two and one hundred microns.

15. The invention as defined in claim 10 wherein said fluid is air.

16. The invention as defined in claim 10 wherein said tooth structure includes exposed tubules and further comprising the step of maintaining impingement of the abrasive material laden fluid stream on the tooth structure for a time sufficient to close said tubules.

17. A method for preparing a tooth structure for bonding with a composite material comprising the steps of:
    creating a fluid stream laden with abrasive material,
    directing said fluid stream towards the tooth structure for a time sufficient so that the abrasive material laden fluid stream impinges upon the tooth structure and roughens the tooth structure,
    wherein said tooth structure includes exposed tubules and further comprising the step of maintaining impingement of the abrasive material laden fluid stream on the tooth structure for a time sufficient to close said tubules.

* * * * *

REEXAMINATION CERTIFICATE (2848th)
United States Patent [19]
Goldsmith

[11] B1 5,275,561
[45] Certificate Issued Apr. 16, 1996

[54] METHOD FOR PREPARING TOOTH STRUCTURE FOR BONDING

[75] Inventor: Daniel S. Goldsmith, West Bloomfield, Mich.

[73] Assignee: American Dental Laser, Inc., Troy, Mich.

Reexamination Request:
No. 90/003,619, Nov. 2, 1994

Reexamination Certificate for:
Patent No.: 5,275,561
Issued: Jan. 4, 1994
Appl. No.: 862,968
Filed: Apr. 3, 1992

[51] Int. Cl.$^6$ .............................. A61C 15/00; A61C 5/00
[52] U.S. Cl. ............................................. 433/216; 433/215
[58] Field of Search .................................. 433/215, 216, 433/88

[56] References Cited

U.S. PATENT DOCUMENTS 4,941,298  7/1990  Fernwood et al. ................... 51/438
5,203,698  4/1993  Blake et al. ......................... 433/88

OTHER PUBLICATIONS

*The Journal of the American Dental Association*, "Nonmechanical Cavity Preparation", Aug., 1945, Black, pp. 955–965.
*Quintessence International Dental Digest*, Sep. 1981, "Abrasive Etching of the Enamel Surface," M. E. Katora et al., pp. 967–968.
*A Textbook of Operative Dentistry*, 1956, "The Use of Airbrasive," W. H. McGehee, et al., pp. 266–273.
*The Journal of the Michigan State Dental Society*, Feb. 1950, "The Airdent Unit and the Airbrasive Technic," W. R. Mann, pp. 23–28.
*The Journal of the American Dental Association*, Nov. 1951, "Analysis of Airbrasive Procedures in Dental Practice," S. Epstein, pp. 573–582.
*The Journal of the New Jersey State Dental Society*, Jul. 1952, "The Airdent and I," A. R. Taylor, pp. 13–14.
*Journal of Dental Research*, Aug. 1952, "Proceedings of the Thirteenth Annual Meeting," H. B. Robinson, pp. 455, 504–505.
*The Journal of the American Dental Assoc.*, Mar. 1953, "Evaluation of the Airdent Unit: Preliminary Report," A. H. Morrison, pp. 298–303.
*Journal of Dental Research*, Oct. 1954, "Proceedings of the Thirty–Second General Meeting," H. B. Robinson, pp. 637–666.
*The Journal of the American Dental Association*, Oct. 1954, "The Effect of High Speed Burs, Diamond Instruments and Air Abrasive in Cutting Tooth Tissue," F. A. Peyton et al., pp. 426–435.
*British Dental Journal*, Dec. 7, 1954, "The Abrasive Technique," G. E. Myers, pp. 291–295.
*The Journal of the American Dental Association*, Apr. 1955, "Appln. and Revaluation of Air Abrasive Technic," R. B. Black, pp. 409–414.

*Primary Examiner*—Cary E. O'Connor

[57] ABSTRACT

The present invention discloses a method for preparing tooth structure, such as dentin and enamel, for bonding with a composite material. The method includes the steps of creating a fluid stream laden with an abrasive material, such as aluminum oxide. The fluid stream is directed towards the tooth structure so that the abrasive material laden fluid stream impinges upon the tooth structure and roughens it for enhanced bonding with composite material.

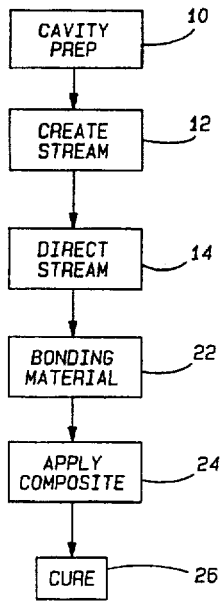

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, lines 57–58:
*Between one and fifteen grams per minute of abrasive material is variably metered into the fluid stream.*

AS A RESULT OF REEXAMINATION, IT HAS BEEN DETERMINED THAT:

The patentability of claim 17 is confirmed.

Claims 5 and 11 having been finally determined to be unpatentable, are cancelled.

Claims 1, 6 and 10 are determined to be patentable as amended.

Claims 2–4, 7–9 and 12–16, dependent on an amended claim, are determined to be patentable.

New claims 18 and 19 are added and determined to be patentable.

1. A method for preparing a tooth structure for bonding with a composite material comprising the steps of:
   creating a fluid stream laden with abrasive material,
   directing said fluid stream towards the tooth structure for a time sufficient so that the abrasive material laden fluid stream impinges upon the tooth structure and roughens the tooth structure *wherein said creating step comprises the step of variably metering abrasive material into the fluid stream, and*
   *wherein said metering step comprises the step of metering between one gram per minute and fifteen grams per minute of abrasive material into the fluid stream,*
   *wherein said fluid is air.*

6. The invention as defined in claim [5] *1* wherein said step of creating a fluid stream comprises the step of using a compressed air source and varying the pressure of the compressed air source.

10. A method for restoration of tooth structure using a composite comprising the steps of:
   creating a fluid stream laden with abrasive material,
   directing said fluid stream towards the tooth structure for a time sufficient so that the abrasive material laden fluid stream impinges upon the tooth structure and roughens the tooth structure,
   thereafter applying a bonding material on the tooth structure that has been roughened,
   thereafter applying composite to the bonding material, and
   curing the bonding material,
   *wherein said bonding material applying step is performed immediately following said directing step.*

*18. A method for preparing a tooth structure for bonding with a composite material comprising the steps of:*
   *creating a fluid stream laden with abrasive material,*
   *directing said fluid stream towards the tooth structure for a time sufficient so that the abrasive material laden fluid stream impinges upon the tooth structure and roughens the tooth structure wherein said creating step comprises the step of variably metering abrasive material in the fluid stream, and*
   *wherein said metering step comprises the step of metering between one gram per minute and fifteen grams per minute of abrasive material into the fluid stream,*
   *wherein said tooth structure includes exposed tubules and further comprising the step of maintaining impingement of the abrasive material laden fluid stream on the tooth structure for a time sufficient to close said tubules.*

*19. A method for restoration of tooth structure using a composite comprising the steps of:*
   *creating a fluid stream laden with abrasive material,*
   *directing said fluid stream towards the tooth structure for a time sufficient so that the abrasive material laden fluid stream impinges upon the tooth structure and roughens the tooth structure,*
   *thereafter applying a bonding material on the tooth structure that has been roughened,*
   *thereafter applying composite to the bonding material, and*
   *curing the bonding material,*
   *wherein said tooth structure includes exposed tubules and further comprising the step of maintaining impingement of the abrasive material laden fluid stream on the tooth structure for a time sufficient to close said tubules.*

\* \* \* \* \*